US009562992B2

(12) United States Patent
Watanabe (10) Patent No.: US 9,562,992 B2
(45) Date of Patent: *Feb. 7, 2017

(54) FLUORESCENCE INFORMATION READING DEVICE AND FLUORESCENCE INFORMATION READING METHOD (71) Applicant: Sharp Kabushiki Kaisha, Osaka-shi, Osaka (JP)

(72) Inventor: Yukio Watanabe, Osaka (JP)

(73) Assignee: Sharp Kabushiki Kaisha, Sakai (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/373,646

(22) PCT Filed: Nov. 29, 2012

(86) PCT No.: PCT/JP2012/080853
§ 371 (c)(1),
(2) Date: Jul. 22, 2014

(87) PCT Pub. No.: WO2013/111446
PCT Pub. Date: Aug. 1, 2013

(65) Prior Publication Data
US 2015/0008338 A1   Jan. 8, 2015

(30) Foreign Application Priority Data

Jan. 26, 2012   (JP) .................. 2012-014183

(51) Int. Cl.
*G02B 19/00* (2006.01)
*G02B 3/00* (2006.01)
(Continued)

(52) U.S. Cl.
CPC ............. *G02B 3/00* (2013.01); *G01N 21/6452* (2013.01); *G01N 21/6486* (2013.01);
(Continued)

(58) Field of Classification Search
CPC .................. G02B 3/00; G02B 19/0047; G01N 2021/6478; G01N 2021/6439; G01N 2201/06113; G01N 2201/101
See application file for complete search history.

(56) References Cited

U.S. PATENT DOCUMENTS 5,528,050 A  *  6/1996  Miller et al. .................. 250/585
5,900,640 A       5/1999  Ogura
(Continued)

FOREIGN PATENT DOCUMENTS

EP    0 814 593 A2   12/1997
JP    10-003134 A    1/1998
(Continued)

OTHER PUBLICATIONS

Official Communication issued in International Patent Application No. PCT/JP2012/080853, mailed on Feb. 12, 2013.

*Primary Examiner* — David Porta
*Assistant Examiner* — Shun Lee
(74) *Attorney, Agent, or Firm* — Keating & Bennett, LLP (57) ABSTRACT Sensitivity is increased by enhancing the fluorescence collection efficiency while suppressing the increase in size of an objective lens. An objective lens 17 is structured to have a convex lens part 26 in a center portion and to have a truncated conical cylindrical body 27 around the convex lens part 26. Therefore, a fluorescence component b having too wide an emission angle to fit in the convex lens part 26, of fluorescence emitted from a sample 16, can be collected by total reflection on an outer peripheral surface 27b of the cylindrical body 27. Thus, even light having too wide an emission angle to be collected by a normal convex lens can be collected. As a result, it is possible to suppress the increase in size of the objective lens, to enhance the fluorescence collection efficiency, and to prevent the S/N ratio from being decreased by the existence of undetected fluo- (Continued)

rescence that is blocked by a prism 20. This can realize a fluorescence information reading device having high sensitivity.

2 Claims, 4 Drawing Sheets

(51) Int. Cl.
  G01N 21/64 (2006.01)
  F21V 8/00 (2006.01)
(52) U.S. Cl.
  CPC ....... G02B 19/0047 (2013.01); *G01N 21/645* (2013.01); *G01N 2021/6439* (2013.01); *G01N 2021/6478* (2013.01); *G01N 2201/06113* (2013.01); *G01N 2201/101* (2013.01); *G02B 6/0035* (2013.01); *G02B 19/0028* (2013.01)

(56) References Cited

U.S. PATENT DOCUMENTS

| | | | |
|---|---|---|---|
| 9,006,687 B2* | 4/2015 | Watanabe | 250/458.1 |
| 2007/0153368 A1* | 7/2007 | Vucinic et al. | 359/368 |
| 2011/0270585 A1* | 11/2011 | Chen | G02B 27/30 |
| | | | 703/1 |

FOREIGN PATENT DOCUMENTS

| | | |
|---|---|---|
| JP | 2000-162126 A | 6/2000 |
| WO | 03/085387 A1 | 10/2003 |
| WO | 2007/041458 A2 | 4/2007 |

\* cited by examiner

FLUORESCENCE INFORMATION READING DEVICE AND FLUORESCENCE INFORMATION READING METHOD

TECHNICAL FIELD

The present invention relates to a fluorescence information reading device and a fluorescence information reading method that read two-dimensionally distributed fluorescent labels.

BACKGROUND ART

A fluorescence detection system utilizing fluorochrome as a labeling substance has hitherto been widely used in the fields of biochemistry and molecular biology. The use of this fluorescence detection system allows evaluations, for example, analysis of genetic sequence and genetic mutation and polymorphism, and separation and identification of proteins. Thus, the fluorescence detection system is utilized for development of medicines as an example.

As the above-described evaluation method utilizing fluorescent labeling, there is often used a method in which biological compounds, such as proteins, are distributed in a gel by electrophoresis and the distribution of the biological compounds is acquired by fluorescence detection. In the electrophoresis, electrodes are set in a solution such as a buffer solution, and an electric field gradient is produced in the solution by the application of direct current. At this time, when protein, DNA (Deoxyribonucleic acid), and RNA (ribo nucleic acid) having charge exist in the solution, molecules having a positive charge are attracted to a cathode and molecules having a negative charge are attracted to an anode. Thus, biomolecules can be separated.

Two-dimensional electrophoresis serving as one evaluation method using the above-described electrophoresis is an evaluation method in which biomolecules are two-dimensionally distributes in a gel by combining two kinds of electrophoresis methods, and is considered as the most effective method for proteomic analysis.

As the electrophoresis methods to be combined, for example, two kinds of methods are mainly used, that is, the methods are "electrofocusing utilizing differences in isoelectric points among individual proteins" is used as the first step, and "SDS-PAGE (sodium dodecyl sulfate-polyacrylamide gel electrophoresis) for separating proteins by the molecular weight" is used as the second step. Fluorochrome is applied to the proteins serving as the biomolecules thus separated before or after electrophoresis.

Further, an image reading device is widely spread in the fields of biochemistry and molecular biology. In the image reading device, a gel support in which the biomolecules (proteins) produced as described above are two-dimensionally distributed is irradiated with excitation light, the intensity of generated fluorescence is acquired, and an image of a fluorescence distribution (protein distribution) is displayed on the basis of the intensity.

As a method for holding the two-dimensional distribution of the biomolecules, a method is also performed, in which the biomolecules are not only held in the gel, but also transferred from the gel to a membrane by utilizing electrophoresis or a capillary action after proteins are separated in the gel. In this case, similarly to image reading using the gel support, the fluorescence distribution on a transfer support formed by the membrane can be imaged by an image reading device.

As the above-described image reading device that reads out an image of a biomolecular distribution from a gel support or a transfer support in which biomolecules are two-dimensionally distributed, Japanese Unexamined Patent Application Publication No. 10-3134 (PTL 1) discloses an image reading device.

In the above-described conventional image reading device, a mirror having a hole in it center portion is mounted on an optical head to be moved in a main scanning direction, and laser light (excitation light) with a wavelength in accordance with the wavelength of a fluorescent substance is applied through the hole of the mirror from a light source to a transfer support on which electrophoresis of denatured DNA labeled by the fluorescent substance is recorded. Then, fluorescence emitted by excitation of fluorochrome in the transfer support is reflected around the hole of the mirror, is photoelectrically converted by a multiplier, and is then detected. In this way, one line of image data is stored in a line buffer. Subsequently, by repeating the above operations while moving the optical head in a sub-scanning direction orthogonal to the main scanning direction, a two-dimensional visible image (fluorescence image) is obtained by an image processing device.

As described above, in the conventional image reading device, excitation light is applied onto the transfer support without using a dichroic mirror. Hence, compared to a method in which excitation light is applied through the dichroic mirror, greater excitation energy can be applied to the transfer support. This can increase the S/N ratio of photoelectrically detected signals (image information).

However, to detect weak fluorescence, a further increase in the S/N ratio is required. Accordingly, Japanese Unexamined Patent Application Publication No. 2000-162126 (PTL 2) discloses an image information reading device as an optical head type image reading device that provides a higher S/N ratio of detected signals than the conventional image reading device.

In this image information reading device, a mirror having a hole in its center portion is mounted on an optical head to be moved in a main scanning direction, and laser light with a wavelength for exciting fluorochrome is applied upward through the hole of the mirror from a laser light source onto a transfer support in which biogenic substances labeled by the fluorochrome are distributed. Then, fluorescence emitted downward by excitation of the fluorochrome in the transfer support reaches the mirror. In contrast, fluorescence emitted above the transfer support is reflected by an inner surface of a concave mirror, travels downward, passes through the transfer support, and reaches the mirror in the optical head. In this way, both the fluorescences reaching the mirror are reflected around the hole of the mirror, are photoelectrically converted by a multiplier, and are then detected. Thus, one line of image data is stored in a line buffer. By subsequently repeating the above operations while moving the optical head in a sub-scanning direction orthogonal to the main scanning direction, a two-dimensional visible image (fluorescence image) is obtained by an image processing device.

By thus increasing the amount of fluorescence to be detected by the multiplier, the S/N ratio of photoelectrically detected signals (image information) can be increased.

However, the above-described conventional image information reading device has the following problems.

That is, in synchronization with movements of the optical head in the main scanning direction and the sub-scanning direction, the concave mirror disposed above the transfer support also needs to be moved in the same directions. This complicates a moving mechanism for the concave mirror.

Further, the fluorescence is emitted from the transfer support at a wide angle. To efficiently detect the fluorescence, the fluorescence emitted at the wide angle needs to be collected at the multiplier. As a method for collecting fluorescence emitted at a wide angle with as high efficiency as possible, there is a method using an objective lens having high NA (numerical aperture). However, this increases the size of a lens element.

In this case, with the increase in size of the objective lens for collecting fluorescence, the sizes of optical elements set in the way to guide the fluorescence to the multiplier, such as a reflective mirror, a laser-light cut filter, and a light collecting lens, are also increased. For this reason, in the image reading device in which the optical system including the optical head is scanned, the total size increases with the increase in size of the optical elements. Particularly when the detection system including the multiplier is scanned while being entirely mounted on the optical head, the weight of a scanning unit increases. Hence, it is feared that high-speed scanning cannot be achieved.

Further, when the sizes of the used optical elements increase, the number, weight, and size of the wavelength filter and so on are limited, and it is difficult to achieve high function.

CITATION LIST

Patent Literature

PTL 1: Japanese Unexamined Patent Application Publication No. 10-3134
PTL 2: Japanese Unexamined Patent Application Publication No. 2000-162126

SUMMARY OF INVENTION

Technical Problem

Accordingly, an object of the present invention is to provide an optical head type fluorescence information reading device and a fluorescence information reading method that enhance fluorescence collection efficiency while suppressing the increase in size of an objective lens and that achieve high sensitivity.

Solution to Problem

To solve the above problems, a fluorescence information reading device according to the present invention includes:
a light source unit that irradiates a reading object with excitation light for exciting fluorescence;
an objective lens element that transmits the excitation light from the light source unit and collects the fluorescence emitted from the reading object by the irradiation with the excitation light;
a lens that converts the fluorescence collected by the objective lens element into substantially parallel fluorescence;
a wavelength filter on which the substantially parallel fluorescence from the lens is incident, the wavelength filter reducing a light component having a wavelength equal to a wavelength of the excitation light; and
a photodetection element that detects the fluorescence from the filter.

The objective lens element includes a center portion that collects light by refraction, and a peripheral portion located around the center portion to collect light by total reflection.

At least a part of the center portion serves as an excitation-light transmitting portion that transmits the excitation light.

According to the above configuration, the objective lens element for collecting fluorescence from the reading object has, on an outer periphery of the center portion that collects light by refraction and corresponds to a normal convex lens, the peripheral portion for collecting light by total reflection. Therefore, it is possible to collect even light having too wide an emission angle to be collected by the normal convex lens and to enhance the light collection efficiency for higher sensitivity of the photodetection element. For this reason, unlike the above-described conventional image information reading device, it is unnecessary to provide a concave mirror for reflecting fluorescence, which is emitted above the reading object, in a downward direction. Thus, the optical system for detecting the fluorescence can be simplified.

Further, compared to the case in which a convex lens having NA equal to that of the objective lens element is used as the objective lens of the fluorescence information reading device, the diameter of the objective lens element can be reduced. Since the objective lens element collects fluorescence from the reading object and causes the fluorescence to enter the lens, the diameters of the lens, the wavelength filter, and the photodetection element can be reduced. This can make the detection optical system compact.

Further, at least a part of the center portion of the objective lens element serves as the excitation-light transmitting portion that transmits the excitation light. For this reason, compared to the method for applying excitation light through the dichroic mirror, greater excitation energy can be applied to the reading object, and the S/N ratio of signals (image information) detected by the photodetection element can be increased.

Further, fluorescence collected by the objective lens element enters the wavelength filter after being converted into substantially parallel light by the lens. Therefore, even when a filter having a sharp cutoff property is used, degradation of the effect of the wavelength filter can be prevented.

The fluorescence information reading device according to an embodiment includes a scanning module that is driven by a scanning mechanism movable relative to the reading object so as to two-dimensionally scan the reading object.

The light source unit, the objective lens element, the lens, the wavelength filter, and the photodetection element are stored in the scanning module.

According to this embodiment, the light source unit, the objective lens element, the lens, the wavelength filter, and the photodetection element stored in the scanning module for two-dimensionally scanning the reading object are configured compactly. Therefore, the size and weight of the scanning module storing these elements can also be reduced. Further, the scanning mechanism for driving the scanning module is simplified, and this allows high-speed scanning.

In the fluorescence information reading device according to an embodiment, the objective lens element is shaped concentrically with an optical axis.

The optical axis penetrates at least a part of the excitation-light transmitting portion.

According to this embodiment, the excitation-light transmitting portion can be provided around the optical axis of the objective lens element shaped concentrically with the optical axis. Therefore, the excitation light can be caused to be substantially perpendicularly incident on the center portion of the objective lens element, and the incidence of the excitation light can be performed easily.

In the fluorescence information reading device according to an embodiment, the reading object is placed on a light transmissive sample table.

The light source unit, the objective lens element, the lens, the wavelength filter, and the photodetection element are disposed opposed to a surface of the sample table opposite from a surface on which the reading object is placed.

The photodetection element detects the fluorescence emitted from the reading object via the sample table.

According to this embodiment, it is only necessary to simply place the reading object on the sample table, and this allows the reading object to be set up easily. Further, since the objective lens element, the lens, the wavelength filter, and the photodetection element can be made compact, it is possible to suppress the increase in size of the detection optical system due to the increase in distance from the reading object to the objective lens element via the sample table.

A fluorescence information reading method according to the present invention includes:

emitting, from a light source unit, excitation light that excites fluorescence;

applying the excitation light from the light source unit onto a reading object through an excitation-light transmitting portion in a center portion of an objective lens element, the objective lens element having the center portion that collects light by refraction and a peripheral portion located around the center portion to collect light by total reflection;

collecting fluorescence emitted from the reading object by the application of the excitation light on the center portion and the peripheral portion of the objective lens element;

converting the fluorescence collected by the objective lens element into substantially parallel fluorescence by a lens;

reducing a light component having a wavelength equal to a wavelength of the excitation light by a wavelength filter from the substantially parallel fluorescence converted by the lens; and detecting the fluorescence from the wavelength filter by a photodetection element.

According to the above configuration, similarly to the above-described fluorescence information reading device of the present invention, it is possible to collect even light having too wide an emission angle to be collected by a normal convex lens and to enhance the light collection efficiency for higher sensitivity of the photodetection element. Further, it is possible to reduce the diameter of the objective lens element and to make the detection optical system, which includes the lens, the wavelength filter, and the photodetection element, compact. Further, it is possible to increase the S/N ratio of signals (image information) to be detected by the photodetection element. Still further, it is possible to prevent degradation of the effect of the wavelength filter even when a filter having a sharp cutoff property is used.

Advantageous Effects of Invention

As is obvious from the above, according to the fluorescence information reading device and the fluorescence information reading method of the present invention, the objective lens element for collecting fluorescence from the reading object has the peripheral portion for collecting light by total reflection, around the center portion corresponding to the normal convex lens and configured to collect light by refraction. Therefore, it is possible to collect even light having too wide an emission angle to be collected by the normal convex lens, to enhance the light collection efficiency for higher sensitivity of the photodetection element.

Further, compared to a case in which a convex lens having NA equal to that of the objective lens element is used, the diameter of the objective lens element can be decreased. Still further, since the objective lens element collects the fluorescence and causes the fluorescence to enter the lens, the detection optical system including the lens, the wavelength filter, and the photodetection element can be made compact.

Further, at least a part of the center portion of the objective lens element serves as the excitation-light transmitting portion. Hence, compared to the method for applying excitation light through the dichroic mirror, greater excitation energy can be applied to the reading object. This can increase the S/N ratio of signals (image information) to be detected by the photodetection element.

DESCRIPTION OF EMBODIMENTS

The present invention will be described in detail below in conjunction with an illustrated embodiment.

Figure 1:
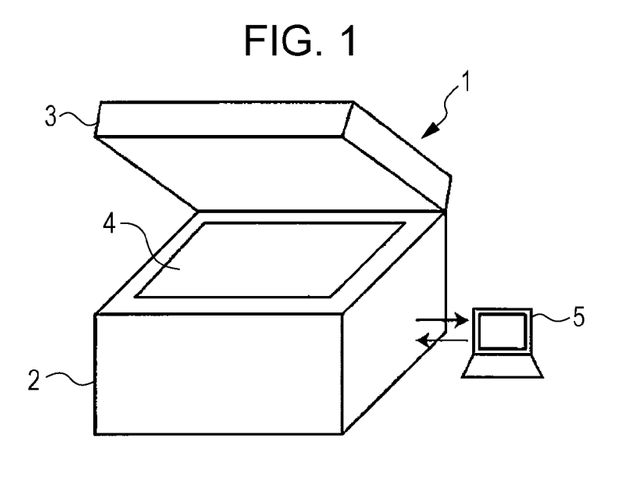
FIG. 1 is an outside view of a fluorescence information reading device according to the present invention.

FIG. 1 is an outside view of a fluorescence information reading device according to an embodiment. A fluorescence information reading device 1 is roughly composed of a body 2 that forms a housing, and a cover 3 that covers an upper surface of the body 2. A sample table 4 made of glass is provided on the upper surface of the body 2. For example, a gel support or a transfer support, such as a membrane, in which biogenic substances labeled by a fluorescent substance (both of the supports are not illustrated) is set as a sample on the sample table 4.

Optical systems are disposed on a lower side of the sample table 4. Excitation light is applied to the sample set on the sample table 4 from below through the sample table 4 by an irradiation optical system, and fluorescence from the sample, which passes through the sample table 4, is detected by a detection optical system. The detection optical system is connected to an external terminal such as a PC (Personal computer) 5, and for example, a measuring condition is controlled from the PC 5. Further, the PC 5 creates a fluorescence image of the sample on the basis of detected data, and displays the created fluorescence image or the like on an incorporated display screen.

Figure 2:
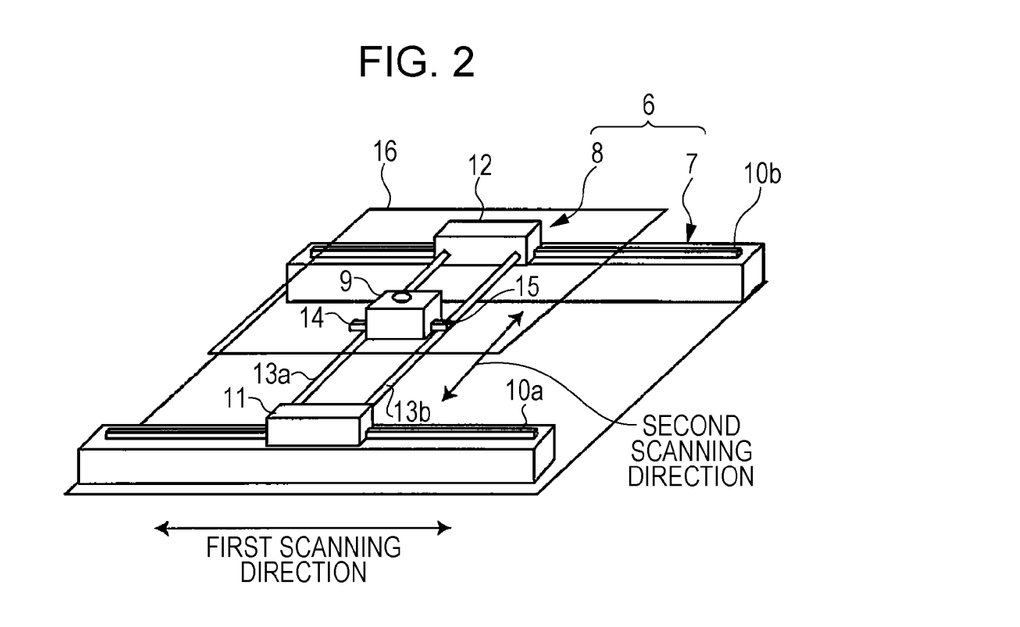
FIG. 2 is an outside view of a scanning stage installed below a sample table in FIG. 1.

FIG. 2 is an outside view of a scanning stage 6 installed below the sample table 4. This scanning stage 6 includes a first stage 7 serving as a base, and a second stage 8 disposed on the first stage 7. On the second stage 8, a scanning module 9 is disposed. The detection optical system for detecting the fluorescence is stored in the scanning module 9.

In the first stage 7 that constitutes the scanning stage 6, two guide rails 10a and 10b are disposed to extend in a first scanning direction and to be opposed to each other with a predetermined space therebetween. The second stage 8 includes a first guide member 11 that is guided by the guide rail 10a of the first stage 7 to reciprocate in the first scanning direction, and a second guide member 12 that is guided by the guide rail 10b to reciprocate in the first scanning direction.

Between the first guide member 11 and the second guide member 12 that constitute the second stage 8, two guide rails 13a and 13b are disposed to extend in a second scanning direction orthogonal to the first scanning direction and to be opposed to each other with a predetermined space therebetween. The scanning module 9 is provided with a first guide member 14 that is guided by the guide rail 13a to reciprocate in the second scanning direction, and a second guide member 15 that is guided by the guide rail 13b to reciprocate in the second scanning direction.

In a scanning method using the scanning stage 6 having the above-described structure, first, the first guide member 11 and the second guide member 12 of the second stage 8 are moved in the first scanning direction while being guided by the guide rails 10a and 10b, respectively, so as to position the second stage 8 relative to the first stage 7. After that, the first guide member 14 and the second guide member 15 of the scanning module 9 are moved in the second scanning direction while being guided by the guide rails 13a and 13b, respectively, so as to position the scanning module 9 relative to the second stage 8. Subsequently, a sample 16 is two-dimensionally scanned by repeating the above operations.

That is, in the embodiment, a moving unit in the first scanning direction is constituted by the guide rails 10a and 10b and the first and second guide members 11 and 12, and a moving unit in the second scanning direction is constituted by the guide rails 13a and 13b and the first and second guide members 14 and 15.

Although a specific description is skipped, further below the scanning stage 6 provided below the sample table 4 and in the body 2 that forms the housing, driving units, such as a motor, a driving belt, ball screws, gears, a control board, a power supply, and wires, are disposed to move the first and second guide members 11 and 12 of the second stage 8 in the first scanning direction and to move the first and second guide members 14 and 15 of the scanning module 9 in the second scanning direction.

That is, in the embodiment, the scanning stage 6 and the driving units constitute the scanning mechanism in the claims.

Figure 3:
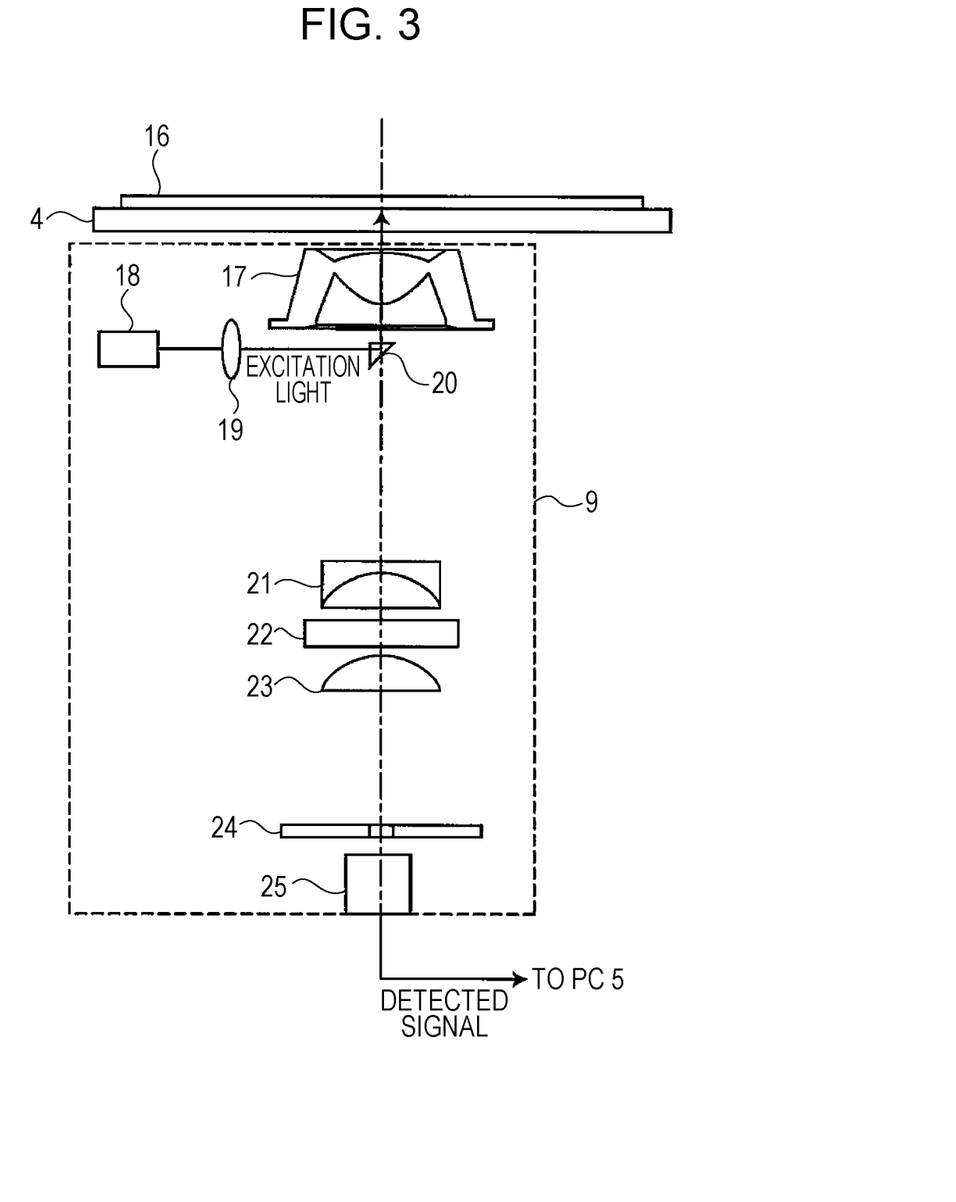
FIG. 3 is a cross-sectional view of a scanning module disposed on a second stage in FIG. 2.

FIG. 3 is a longitudinal sectional view illustrating a schematic structure of the scanning module 9 disposed on the second stage 8. In FIG. 3, an objective lens 17 is disposed in an upper part of the scanning module 9 and near the sample table (glass) 4 to collect fluorescence from a sample 16 set on the sample table 4. Further, a prism 20 is disposed at a position, where the optical axis of the objective lens 17 and the optical axis of a light source 18 of excitation light intersect at right angles, to reflect excitation light, such as laser light, emitted from the light source 18 and collected by a first lens 19 so that the excitation light enters the objective lens 17.

Below the prism 20 on the optical axis of the objective lens 17, a second lens 21 for converting fluorescence from the sample 16 collected by the objective lens 17 into parallel light, a cutting wavelength filter 22 for cutting excitation light, a third lens 23 for collecting fluorescence passing through the wavelength filter 22, and a pinhole 24 for cutting stray light of fluorescence passing through the third lens 23 are disposed in order from a side of the prism 20. Further, below the pinhole 24 on the optical axis of the objective lens 17, a detector 25 is disposed to detect fluorescence passing through the pinhole 24.

In the scanning module 9 having the above-described structure, excitation light emitted from the light source 18 is converged by the first lens 19, is next reflected by the prism 20, passes through the objective lens 17 and the sample table 4, and is collected at one point on a lower surface of the sample 16. In this case, the length of the prism 20 in a longitudinal direction (a direction orthogonal to the optical axis of the first lens 19) is short, and the width thereof in a direction orthogonal to the longitudinal direction is narrow. The excitation light from the light source 18 passes only near the optical axis of the objective lens 17 (an excitation-light transmitting portion).

That is, in the embodiment, the light source 18, the first lens 19, and the prism 20 constitute the light source unit in the claims.

The fluorescence is isotropically emitted around from a portion of the sample 16 irradiated with the excitation light. A component of the emitted fluorescence, which has passed through the sample table 4 made of glass and entered the objective lens 17, passes through the objective lens 17, the second lens 21, the wavelength filter 22, the third lens 23, and the pinhole 24, and is detected by the detector 25. Signals detected by the detector 25 are subjected to processing, for example, AD conversion by an AD converter incorporated therein, and are then transmitted to the PC 5. Thus, a distribution of fluorescence intensities at measuring points on the sample 16 is recorded in, for example, an internal memory.

Here, as described above, the fluorescence that has passed through the objective lens 17 is guided as convergent light toward the second lens 21. Then, the fluorescence is refracted by the second lens 21 so as to become substantially parallel light. Further, the third lens 23 collects the fluorescence. The pinhole 24 is disposed to spatially cut stray light. The wavelength filter 22 for cutting excitation light is disposed in, for example, a rotary folder (not illustrated), and can be replaced with other wavelength filters in accordance with the wavelength of the excitation light.

A detailed description will be given below of the objective lens 17 that characterizes the present application.

Figure 4:
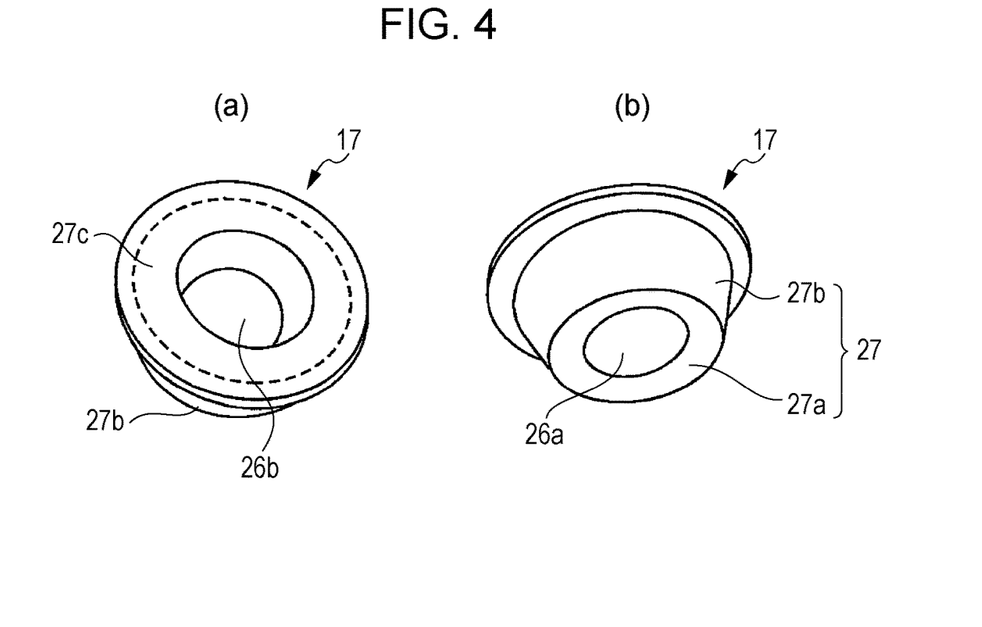
FIG. 4 includes perspective views of an objective lens in FIG. 3.
Figure 5:
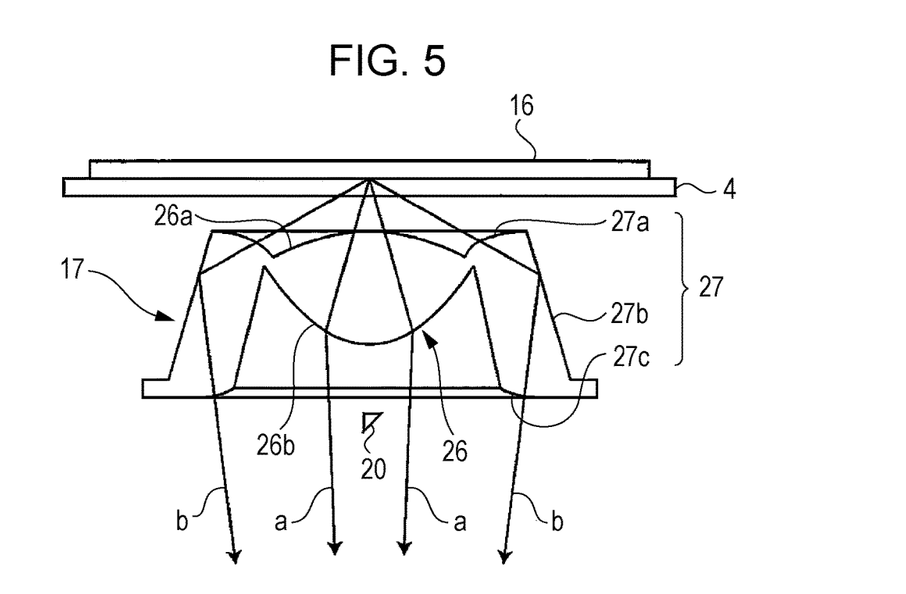
FIG. 5 is a cross-sectional view of the objective lens.

FIG. 4 includes perspective views of the objective lens 17. FIG. 4(a) is a perspective view from the prism 20. FIG. 4(b) is a perspective view from the sample table 4. FIG. 5 is a longitudinal sectional view of the objective lens 17.

As can be seen from FIGS. 4 and 5, the objective lens 17 is shaped like an inverted ashtray. A center portion including the optical axis includes an upper convex surface 26a and a lower convex surface 26b that spherically project along the optical axis, and serves as a convex lens part 26 having a function of a normal convex lens (function of deflecting light only by refraction). As illustrated in FIG. 5, a fluorescence component a with a small emission angle, of fluorescence emitted from the sample 16, passes through the convex lens part 26, and is collected toward the detector 25.

A portion of the objective lens 17 around the lower convex surface 26b (convex lens part 26) serves as a truncated conical cylindrical body 27 opening downward. A fluorescence component b having too wide an emission angle to fit in the convex lens part 26, of the fluorescence emitted from the sample 16, enters the cylindrical body 27 from an upper end surface 27a of the cylindrical body 27, is deflected toward the optical axis by total reflection on an outer peripheral surface 27b of the cylindrical body 27, and is emitted from a lower end surface 27c of the cylindrical body 27 toward the detector 25.

That is, in the embodiment, the convex lens part 26 forms the center portion in the claims, and the cylindrical body 27 forms the peripheral portion.

As described above, light having too wide an emission angle to be collected by the normal convex lens can be collected by totally reflecting, by the outer peripheral surface 27b of the cylindrical body 27, a fluorescence component having too wide an emission angle to fit in the convex lens part 26, of fluorescence emitted from the sample 16. For this reason, sensitivity of the detector 25 can be increased.

The lens element itself can be made more compact than when the objective lens of this fluorescence information reading device 1 is realized by a normal convex lens having an NA equal to that of the objective lens 17.

Figure 6:
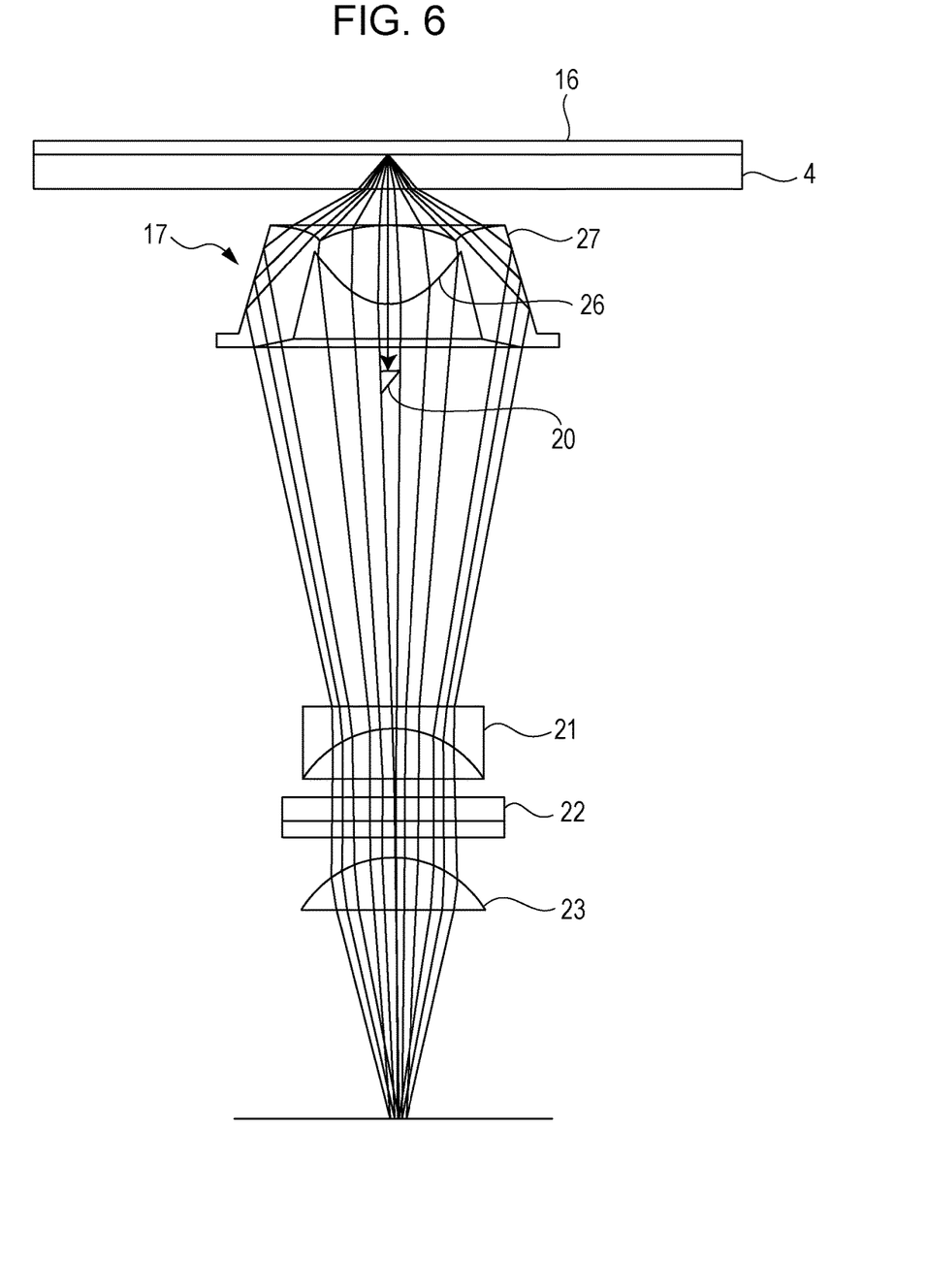
FIG. 6 is a ray diagram of fluorescence from the objective lens to a third lens in FIG. 3.

FIG. 6 is a ray diagram of fluorescence that is emitted from the sample 16 and passes from the objective lens 17 to the third lens 23. Referring to FIG. 6, since an interference filter having a sharp cutoff property is used as the wavelength filter 22, it is necessary to convert incident light on the wavelength filter 22 into parallel light. Accordingly, fluorescence collected through the objective lens 17 is caused to be incident on the wavelength filter 22 after being converted into substantially parallel light by the second lens 21. Here, the fluorescence can be converted into parallel light by the objective lens 17. In this case, however, the beam diameter of fluorescence increases, and this increases the sizes of the second lens 21 and the subsequent optical elements.

Therefore, when the above-described objective lens 17 having the convex lens part 26 in the center portion and the truncated conical cylindrical body 27 around the convex lens part 26 is used, the sizes of the optical elements, that is, the second lens 21, the wavelength filter 22, and the third lens 23 can be reduced, and the size and weight of the scanning module 9 can be reduced.

When the wavelength filter 22 is disposed in the rotary folder, the number of wavelength filters 22 to be mounted can be increased by reducing the size of the wavelength filter 22. This can increase the number of kinds of measurable fluorescence reagents.

A lens having a convex lens part in a center portion and a truncated conical cylindrical body around the convex lens part is disclosed in Japanese Unexamined Patent Application Publication No. 2007-266180 and International Publication No. WO 2008/069143. However, both of these patent literatures relate to a light emitting lens that allows light from a light emitting element, such as an LED, to be emitted forward with high directivity, but do not disclose and suggest the point in that a lens similar to the light emitting lens is used as an objective lens in a fluorescence information reading device and the point in that optical elements of the fluorescence information reading device are reduced in size by using the lens as the objective lens.

As described above, in the embodiment, the sample table 4 made of glass is provided on the upper surface of the body 2 that forms the housing, and for example, a gel support or a transfer support, in which biogenic substances labeled by a fluorescent material are distributed, is set as a sample 16 on the sample table 4. In the scanning module 9 that performs two-dimensional scanning by being moved in the first scanning direction and the second scanning direction by the scanning stage 6 disposed below the sample table 4, the irradiation optical system constituted by the light source 18, the first lens 19, the prism 20, and the objective lens 17 is disposed. The objective lens 17 transmits excitation light emitted from the light source 18, collected by the first lens 19, and reflected by the prism 20 so as to irradiate the sample 16. Then, the objective lens 17 collects fluorescence from the sample 16.

Further, in the scanning module 9, the detection optical system is contained integrally, which is constituted by the second lens 21 for converting fluorescence collected by the objective lens 17 into substantially parallel light, the cutting wavelength filter 22 for cutting excitation light, the third lens 23 for collecting the fluorescence, the pinhole 24 for cutting stray light, and the detector 25 for detecting the fluorescence.

The objective lens 17 is structured to have the convex lens part 26 in the center portion and the truncated conical cylindrical body 27 around the convex lens part 26. Therefore, the fluorescence component b having too wide an emission angle to fit in the convex lens part 26, of the fluorescence emitted from the sample 16, can be totally reflected and collected by the outer peripheral surface 27b of the cylindrical body 27, and even light having too wide an emission angle to be collected by the normal convex lens can be collected. As a result, the light collection efficiency of the fluorescence can be enhanced, and the S/N ratio can be prevented from being decreased by the existence of fluorescence that is blocked by the prism 20 disposed on the optical axis of the objective lens 17 and is not detected by the detector 25. Thus, a fluorescence information reading device having high sensitivity can be realized.

Therefore, according to the embodiment, unlike the above-described conventional image information reading device, it is unnecessary to provide the concave mirror for reflecting fluorescence, which is emitted above the sample 16, in a downward direction and to move the concave mirror in the same direction in synchronization of movement of the scanning module 9. For this reason, the scanning mechanism for two-dimensional scanning is not complicated.

Further, the size of the objective lens 17 can be made smaller than when the fluorescence component b having a wide emission angle is collected by the normal convex lens having high NA. Further, since the objective lens 17 collects fluorescence from the sample 16 and causes the fluorescence to enter the second lens 21, the sizes of the optical elements disposed on the optical path along which the fluorescence is guided to the detector 25, such as the second lens 21, the wavelength filter 22, and the third lens 23, can also be reduced.

By reducing the sizes of the optical elements, such as the objective lens 17, the second lens 21, the wavelength filter 22, and the third lens 23, the weight of the scanning module 9 that incorporates the irradiation optical system and the detection optical system can be reduced. Therefore, it is possible to simplify the structure of the scanning mechanism and to reduce the weight of the scanning mechanism so that the scanning module 9 can perform high-speed scanning. Therefore, it is possible to detect a two-dimensional distribution of fluorescence at a plurality of different positions on the sample 16 at high speed.

As illustrated in FIGS. 4 and 5, the objective lens 17 has a concentric planar shape that is symmetrical with respect to the center axis serving as the optical axis. This center axis overlaps with at least a part of an optical path along which the excitation light reflected by the prism 20 passes. For this reason, compared to the method in which excitation light is applied through the dichroic mirror, greater excitation energy can be applied to the sample 16. This can increase the S/N ratio of signals (information signals) photoelectrically detected by the detector 25.

The sample 16 is set on the light-transmissive sample table 4, and the scanning module 9 including the detector 25 for detecting fluorescence is disposed opposed to a surface of the sample table 4 opposite from a setting surface for the sample 16. The detector 25 detects fluorescence from the sample 16 via the sample table 4. Therefore, it is only necessary to lay the two-dimensional sample 16 flat on the sample table 4, and this allows easy setup of the sample 16. Further, the detector 25 for fluorescence can be disposed on the same side of the sample table 4 as the light source 18 for excitation light, and the light source 18 can be disposed in the scanning module 9. Thus, the total size of the optical system can be reduced.

While excitation light is applied from the single light source 18 to the sample 16 in the above embodiment, a plurality of light sources may be provided to selectively apply excitation lights having different wavelengths in accordance with the wavelength of the fluorescent substance that labels biogenic substances on the sample 16.

The wavelength filter 22 for cutting excitation light is disposed in the rotary holder or the like, and can be replaced with other wavelength filters in accordance with the wavelength of the excitation light. However, the present invention is not limited thereto, and a plurality of wavelength filters can be stacked movably forward and backward, and a filter for a target wavelength can be moved forward in accordance with the wavelength of the excitation light.

REFERENCE SIGNS LIST

1: fluorescence information reading device
2: body
4: sample table
5: PC
6: scanning stage
7: first stage
8: second stage
9: scanning module
10a, 10b, 13a, 13b: guide rail
11, 14: first guide member
12, 15: second guide member
16: sample
17: objective lens
18: light source
19: first lens
20: prism
21: second lens
22: wavelength filter
23: third lens
24: pinhole
25: detector
26: convex lens part
26a: upper convex surface
26b: lower convex surface
27: cylindrical body

The invention claimed is:

1. A fluorescence information reading device, comprising:
a light source that irradiates a reading object with excitation light for exciting fluorescence;
an objective lens element that transmits the excitation light from the light source and collects the fluorescence emitted from the reading object by the irradiation with the excitation light;
a lens that converts the fluorescence collected by the objective lens element into substantially parallel fluorescence;
a wavelength filter on which the substantially parallel fluorescence from the lens is incident, the wavelength filter reducing a light component having a wavelength equal to a wavelength of the excitation light; and
a photodetection element that detects the fluorescence from the filter; wherein
the objective lens element is a single monolithic member that includes a center portion that collects light by refraction, the center portion including an upper convex surface and a lower convex surface that spherically projects along an optical axis, the lower convex surface projecting towards the photodetection element, and a peripheral portion located around the center portion to collect light by total reflection, the peripheral portion projects farther towards the photodetection element than the lower convex surface;
at least a portion of the center portion serves as an excitation-light transmitting portion that transmits the excitation light;
the peripheral portion includes a truncated conical body opening downward towards the photodetection element, the truncated conical body including an upper end surface, an outer peripheral surface, and a lower end surface, wherein the fluorescence enters the truncated conical body from the upper end surface and is deflected towards the optical axis on the outer peripheral surface and emitted from the lower end surface, and
a portion of the upper convex surface is on a same plane as a portion of the upper end surface.

2. A fluorescence information reading method, comprising:
emitting, from a light source, excitation light that excites fluorescence;
applying the excitation light from the light source onto a reading object through an excitation-light transmitting portion in a center portion of an objective lens element, the objective lens element is a single monolithic member having the center portion that collects light by refraction and a peripheral portion located around the center portion to collect light by total reflection;
collecting fluorescence emitted from the reading object by the application of the excitation light on the center portion and the peripheral portion of the objective lens element;
converting the fluorescence collected by the objective lens element into substantially parallel fluorescence by a lens;
reducing a light component having a wavelength equal to a wavelength of the excitation light by a wavelength filter from the substantially parallel fluorescence converted by the lens; and
detecting the fluorescence from the wavelength filter by a photodetection element; wherein
the center portion includes an upper convex surface and a lower convex surface that spherically project along an optical axis, the lower convex surface projecting towards the photodetection element;
the peripheral portion projects farther towards the photodetection element than the lower convex surface;
the peripheral portion includes a truncated conical body opening downward towards the photodetection element, the truncated conical body including an upper end surface, an outer peripheral surface, and a lower end surface, wherein the fluorescence enters the truncated conical body from the upper end surface and is deflected towards the optical axis on the outer peripheral surface and emitted from the lower end surface, and a portion of the upper convex surface is on a same plane as a portion of the upper end surface.

* * * * *